(12) United States Patent
Rombach

(10) Patent No.: US 8,690,942 B2
(45) Date of Patent: Apr. 8, 2014

(54) INTRA-OCULAR ARTIFICIAL LENS FOR IRIS-DRIVEN ACCOMMODATION

(75) Inventor: Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 869 days.

(21) Appl. No.: 11/914,276

(22) PCT Filed: May 11, 2006

(86) PCT No.: PCT/NL2006/050114
§ 371 (c)(1),
(2), (4) Date: Apr. 9, 2008

(87) PCT Pub. No.: WO2007/027091
PCT Pub. Date: Mar. 8, 2007

(65) Prior Publication Data
US 2008/0215146 A1    Sep. 4, 2008

(30) Foreign Application Priority Data

May 13, 2005 (NL) ...................................... 1029037
Jul. 18, 2005 (NL) ...................................... 1029548

(51) Int. Cl.
*A61F 2/16* (2006.01)
(52) U.S. Cl.
USPC ........................................................ 623/6.32
(58) Field of Classification Search
USPC ................................................. 623/6.11–6.62
See application file for complete search history.

(56) References Cited

U.S. PATENT DOCUMENTS

| | | | |
|---|---|---|---|
| 3,305,294 A | 2/1967 | Alvarez | |
| 4,206,518 A * | 6/1980 | Jardon et al. | 623/6.44 |
| 4,373,218 A | 2/1983 | Schachar | |
| 4,702,244 A * | 10/1987 | Mazzocco | 606/107 |
| 4,976,732 A | 12/1990 | Vorosmarthy | |
| 4,994,082 A | 2/1991 | Richards et al. | |
| 6,063,116 A * | 5/2000 | Kelleher | 623/6.56 |
| 6,197,019 B1 * | 3/2001 | Peyman | 606/5 |
| 6,616,691 B1 * | 9/2003 | Tran | 623/6.11 |
| 2002/0042653 A1 * | 4/2002 | Copeland et al. | 623/6.6 |

(Continued)

FOREIGN PATENT DOCUMENTS

| | | |
|---|---|---|
| EP | 0162573 A2 | 11/1985 |
| EP | 0329981 A1 | 8/1989 |

(Continued)

OTHER PUBLICATIONS

Search Report and Written Opinion; International Patent Application No. PCT/NL2006/050114; May 8, 2008.

*Primary Examiner* — William H. Matthews
(74) *Attorney, Agent, or Firm* — Jason A. Bernstein; Barnes & Thornburg LLP

(57) ABSTRACT

An intra-ocular artificial lens with variable optical strength, wherein the artificial lens comprises two optical elements which are movable relative to each other in a direction extending transversely of the optical axis, wherein the optical elements have a form such that in different relative positions they together have different optical strengths, wherein the movable optical elements are connected to positioning means which are adapted for coupling to the iris of the eye for the purpose of driving. This measure makes use of the fact that one or both of the optical elements can be displaced relative to each other through the driving of the natural orbicularis muscle of the iris in order to obtain an accommodating function.

20 Claims, 4 Drawing Sheets

(56) References Cited

U.S. PATENT DOCUMENTS

| | | |
|---|---|---|
| 2002/0193877 A1 * | 12/2002 | Hoffmann et al. ............ 623/6.43 |
| 2003/0199976 A1 * | 10/2003 | Portney ........................ 623/6.17 |
| 2005/0064010 A1 | 3/2005 | Cooper et al. |
| 2005/0149185 A1 * | 7/2005 | Cukrowski ................... 623/6.32 |

FOREIGN PATENT DOCUMENTS

| | | |
|---|---|---|
| EP | 0435525 A2 | 7/1991 |
| JP | 5194212 | 8/1993 |
| NL | 1028496 | 9/2006 |
| NL | 1029041 | 9/2006 |
| WO | 9520926 A1 | 8/1995 |
| WO | 9962434 A1 | 12/1999 |
| WO | 0150984 A1 | 7/2001 |
| WO | 03017873 A1 | 3/2003 |
| WO | 2005011813 A2 | 2/2005 |
| WO | 2005027906 A1 | 3/2005 |
| WO | 2005084587 A2 | 9/2005 |

* cited by examiner

FIG. 5
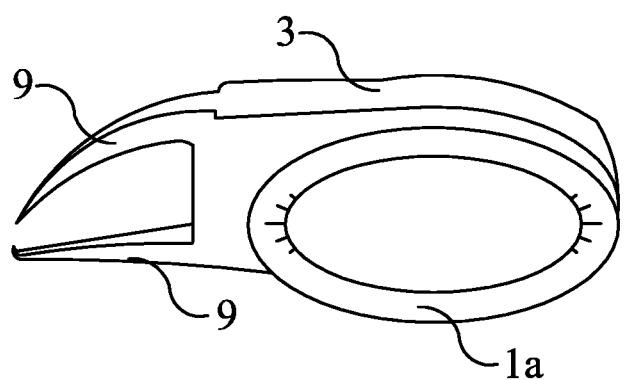
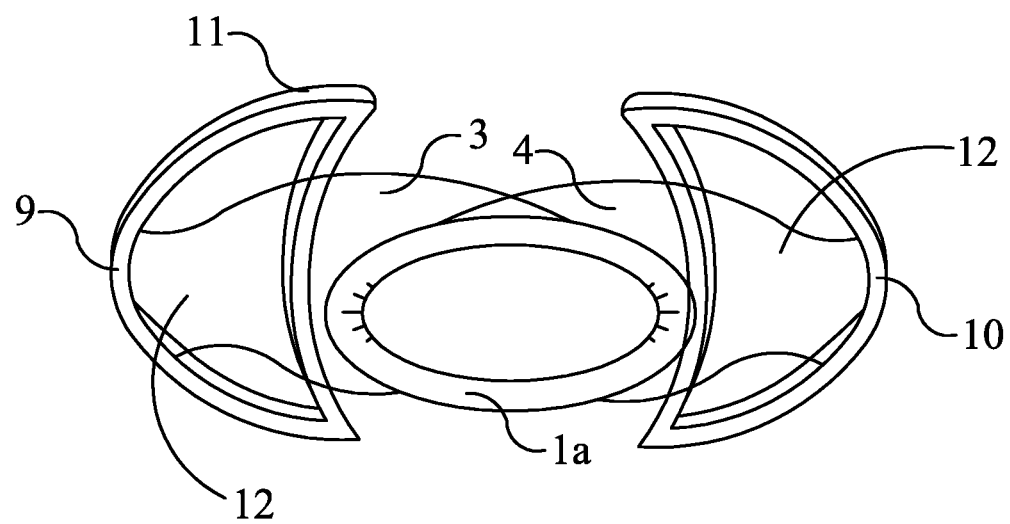
FIG. 6

FIG. 7
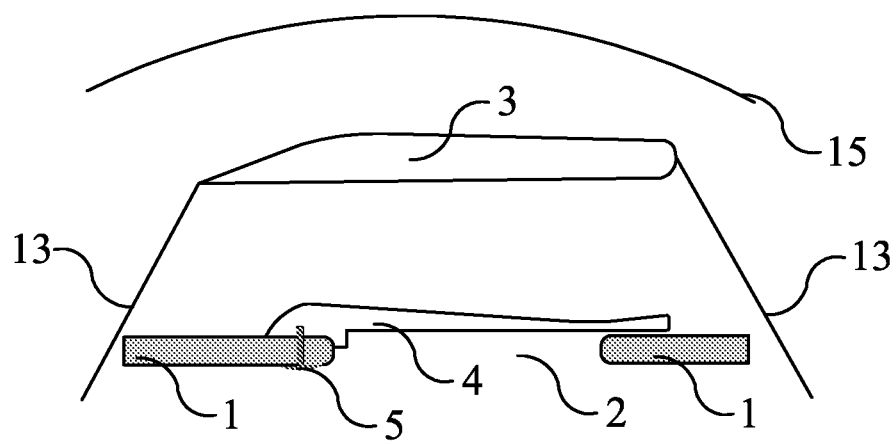
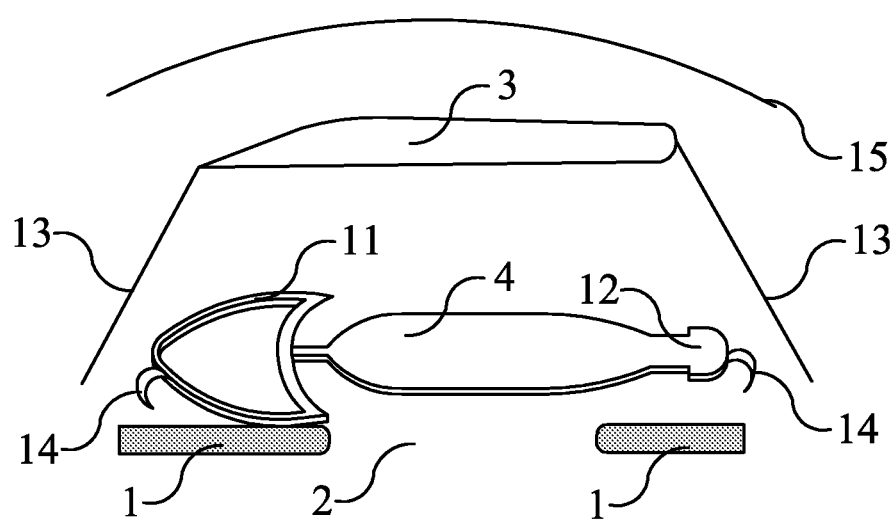
FIG. 8

INTRA-OCULAR ARTIFICIAL LENS FOR IRIS-DRIVEN ACCOMMODATION

PRIORITY CLAIM

This patent application is a U.S. National Phase of International Application No. PCT/NL2006/050114, filed May 11, 2006, which claims priority to Netherlands Patent Application No. 1029037, filed May 13, 2005, and Netherlands Patent Application No. 1029548, filed Jul. 18, 2005, the disclosures of which are incorporated herein by reference in their entirety.

FIELD

The present disclosure relates to an intra-ocular artificial lens with variable optical strength, wherein the artificial lens comprises at least two optical elements, at least two of which are movable relative to each other in a direction extending transversely of the optical axis, wherein the optical elements have a form such that in different relative positions of the optical elements the artificial lens has different optical strengths. The optical elements comprise positioning means for positioning the optical elements in the eye and on the iris for the purpose of driving at least one of the optical elements in order to perform a movement relative to the other optical element.

BACKGROUND

Such intra-ocular artificial lenses for implantation in the eye form the subject matter of Netherlands Patent Application Nos. 1028496 and 1029041 and International Patent Application No. PCT/NL2005/000153.

In these documents, the intra-ocular artificial lens is driven by the orbicularis oculi muscle, which in the natural situation drives the accommodating function of the natural eye lens. PCT/NL2005/000153 discusses the principle of variable optical power of lenses. That document refers to and incorporates by reference U.S. Pat. No. 3,305,294, which describes the optical thickness of a lens element by the equation $t=A(xy^2+x^3/3)$, where t is the optical thickness of the optical element in the direction of the optical axis, x is the coordinate in the direction of the motion of the optical elements, y is the coordinate in the direction perpendicular to the optical axis and to the x-direction, and A is a constant.

The eye lens lies quite deeply in the eye, however, so that according to the prior art replacement of the eye lens by the accommodating eye lens requires an operation wherein it is necessary to operate quite deeply in the eye. The feature of the present disclosure provides such an intra-ocular artificial lens, wherein the arranging thereof requires operating less deeply in the eye.

SUMMARY

The present disclosure describes several exemplary embodiments of the present invention.

One aspect of the present disclosure provides an intra-ocular artificial lens with variable optical strength, wherein the artificial lens comprises at least two optical elements, at least two of which are movable relative to each other in a direction extending transversely of the optical axis, wherein the optical elements have a form such that in different relative positions of the optical elements the artificial lens has different optical strengths, wherein at least one of the movable optical elements is connected to positioning means which are adapted for coupling to the iris of the eye for the purpose of driving.

Another aspect of the present disclosure provides a method for providing an accommodating intra-ocular artificial lens, the method comprising arranging an optical element on the cornea via a laser treatment.

An artificial lens according to the present disclosure functions generally in combination with a fixed lens in the lens capsule. This fixed lens can be either a natural, inelastic and presbyopic lens or a non-accommodating artificial lens placed as a consequence of, for instance, cataracts. An artificial lens according to the present disclosure could also function without a fixed lens in the lens capsule, although the optical properties will then, of course, be different compared to the previous example.

This feature is achieved by such an intra-ocular eye lens wherein at least one of the movable optical elements is connected to positioning means which are adapted for coupling to the iris of the eye for the purpose of driving.

This measure makes use of the fact that one or both of the optical elements can be displaced relative to each other through the driving of the natural orbicularis muscle of the iris in order to obtain an accommodating function.

The natural lens will, in practice, often be inelastic due to presbyopia (long-sightedness), and the artificial lens will often be a lens which has been implanted by an ophthalmic surgeon to replace the natural lens which has become opaque as a result of cataracts.

In the natural eye, lens accommodation of the eye takes place as follows. The orbicularis oculi muscle is contracted for near vision; the lens capsule, the natural casing of the natural eye lens, dilates whereby the natural eye lens, as a result of its elasticity, takes on its natural convex form. For distance vision, the orbicularis muscle dilates, the lens capsule is contracted and the natural eye lens is pulled flatter. The natural rest position of the natural eye lens is, therefore, near vision, and the natural rest position of the orbicularis muscle is, conversely, distance vision. In the case of presbyopic patients (long-sighted people; people with reading glasses; practically anyone older than 35 years of age), the natural lens has hardened, still transmits light but no longer accommodates. These people can generally focus on distant objects but not on near objects. In the case of patients with cataracts, the natural lens is opaque and will have to be removed by the ophthalmic surgeon and replaced by an artificial lens.

The iris has a natural central opening, the pupil, which becomes smaller or larger depending on the amount of light reaching the eye from outside. The pupil becomes small at a high light intensity, and the pupil enlarges at a low light intensity. The amount of light finally incident upon the retina can thus be kept relatively constant for optimum functioning of the retina. The iris is built up from an elastic tissue extending in radial direction and consisting of fibers. Situated in this fibrous tissue are melanocytes which produce melanosomes. These melanosomes are filled with melanin which determines the color of the iris and which makes the iris largely opaque to light. The patterns in which these melanosomes are deposited largely determine the color of the iris. Situated centrally in the iris is an orbicularis muscle which controls the change in pupil size.

Experience has shown that the iris of the eye takes on a small diameter in the case of near vision, for instance, during reading, and a large diameter in the case of distance vision, for instance, during driving at night. This effect of the iris can, therefore, also be used to drive the accommodation of the eye. This principle is already being applied now in several existing lenses, particularly for patients with cataracts, where the natural lens is replaced by a special, non-accommodating artificial lens.

According to a first exemplary embodiment, the positioning means are adapted to cause the optical elements to make a translating movement relative to each other during movement of the iris. A simple construction of the positioning means is hereby obtained.

According to another exemplary embodiment, the positioning means are adapted to cause the optical elements to make a rotating movement relative to each other during movement of the iris. The construction of the positioning means also becomes relatively simple. It is also possible to make use of a composite form of movement. In the above exemplary embodiments the two optical elements usually shift relative to each other over equal distances during the change in diameter of the iris.

Yet another preferred exemplary embodiment provides the measure that the positioning means are adapted to fix one of the optical elements relative to the eyeball and to drive one of the other optical elements during movement of the iris. This latter movable element, in combination with the fixed element, provides for the variation in focal distance of the whole construction driven by the iris. This principle can be embodied by combining one of the optical elements with a construction which supports in the corners of the anterior chamber (a chamber corner-supported construction).

A variant of the above exemplary embodiments provides the measure that the positioning means are connected to mechanical arresting means for limiting the stroke of the optical elements. These arresting means can be placed at random, structurally attractive locations on or around the optical elements. The arresting means define the rest position of the intra-ocular artificial lens. The arresting means can be placed so as to be active on both sides of the working area, so that the arresting means serve to define an area over which the optical elements can be moved. These arresting protrusions can be of a light construction since the iris and the intra-ocular lens are driven only by a weak orbicularis muscle. Arresting protrusions can be applied in all the above and subsequent exemplary embodiments.

The positioning means are preferably adapted for forming by the optical elements at a small pupil diameter of a lens with a high dioptric value and for forming by the optical elements at a large pupil diameter of a lens with a low dioptric value. The optical elements are adapted to have the optical strength for near vision, i.e., a high dioptric strength, at a high light intensity and so a small opening of the pupil. The optical elements are also adapted to have the optical strength for distance vision, i.e., a low dioptric strength, at a low light intensity and so a large opening of the pupil.

One or more optical elements can be adapted so as to also have negative optical strength in order to compensate a myopia (near-sightedness) in a patient.

Other optical modifications can also be made to compensate other aberrations, such as astigmatic aberrations and other order aberrations of the individual eye.

The optical elements are preferably arranged at a distance from each other, each on one side or both on one side of the iris.

The present disclosure provides the measure that the optical elements are drivable by the iris. Use is preferably made for this purpose of the measure that the positioning means of at least one of the optical elements is connected to the iris. This does, after all, represent an easy way to couple the optical elements to the driving member, the iris.

It is structurally simple when the optical elements are connected to the iris on one side. The configuration hereby becomes simpler, particularly when the positioning means can be connected to the iris only on the front side by a surgical treatment. It is possible here to apply a configuration wherein the optical elements are placed on either side of the iris. The positioning means of one of the optical elements then extend through the opening of the iris and are connected to the iris on the other side.

A plurality of connections per optical element can ensure that the optical elements can move reciprocally in only one direction and cannot rotate radially. The tissue from which the iris is built up is well suited to such a construction, since this tissue also consists of elastic fibers extending in a radial direction. The advantage of such a construction is that the optical elements can move completely freely of each other and can thus be set into motion by the weak orbicularis muscle of the iris.

The positioning means are preferably connected to the iris by means of a nail, clamp or (claw) hook connection. Other connections engaging on or form-fitting on the iris are by no means precluded.

The heads of the nails are preferably situated on the rear side (inner side) of the iris. The heads are hereby less visible, this being important from a cosmetic viewpoint.

A specific preferred exemplary embodiment provides the measure that the nail or nails have a form such that they are elastically adaptable to a change in the diameter of the pupil. The iris is a dynamic whole. The diameter of the iris deforms as a result of contracting and dilating of the orbicularis muscle. It should, however, be noted that when one of the elements is fixed to the rear side of the iris, the element must be separate from the lens capsule if the natural lens is still present.

Another alternative provides an exemplary embodiment wherein the optical elements are clamped via a clamp connection to the edge of the pupil, being the opening in the iris, this on or around the muscle which brings about the contraction of the pupil with optionally a light supporting construction extending to the inner side of the iris and the outer side of the pupil. The clamp connection must be sufficiently wide to prevent rotation of the optical elements in a radial direction. In this exemplary embodiment, the optical elements can also move completely freely of each other.

Yet another alternative provides an exemplary embodiment wherein the optical elements are hooked into the fibrous tissue of the iris via a (claw) hook connection close to the edge of the pupil, this on or outside the muscle which brings about contraction of the pupil. In this exemplary embodiment both optical elements can be constructed such that they both hook on the front side of the iris. This clamp connection must be sufficiently wide to prevent rotation in a radial direction. In this exemplary embodiment, the optical elements can displace completely freely of each other. Both optical elements can also be joined together in a construction which provides for individual displacement of the optical elements via a spring connection. This construction is comparable to the accommodating intra-ocular lens described in Netherlands Patent Application Nos. 1029037 and 1029041 and International Patent Application No. PCT/NL2005/000153. Here only one element of the accommodating artificial lens can be fixed to the iris, while another optical element independently occupies a fixed position relative thereto.

As already stated above, the present disclosure requires the presence of a connection between the connecting elements and the part of the iris co-displacing with the central orbicularis muscle. It is, therefore, important to limit extending of connections in a radial direction in all exemplary embodiments since the central part, the inner side, of the iris moves through a considerably greater distance than the outer side of the iris.

The claws or hooks of the connections to the optical elements are preferably situated on the front side of the iris; this results in a better accessibility, and thereby placeability, of the auxiliary means.

A single element of such a construction can also be used in combination with a fixed element of any form whatever for the present application of an iris-driven accommodating intra-ocular lens. This fixed element can be formed by an optical element with a fixed position between cornea and iris. It is the case for all exemplary embodiments that the intra-ocular artificial lens must be placed during a surgical operation. The pupil has a maximum diameter during the operation. The above-stated exemplary embodiments of an intra-ocular lens can all be inserted via the anterior chamber. This makes implanting of such an iris-driven intra-ocular artificial lens a relatively simple surgical treatment.

It is, however, also possible to place the element with a fixed position between the iris and the lens capsule. With the correct choice of materials for the artificial lens, this placement can then come into contact with the lens capsule without medical drawbacks worthy of mention.

It is, however, also possible to make use of existing transparent structures in the eye in order to provide the function of one of the optical elements. This requires arranging a surface on these structures in order to have the optical properties of the structure fulfill the desired function. It is thus possible to use the easily accessible cornea for this purpose. So-called laser eye surgery is in general use. Lasek and femtosecond laser equipment, in particular, can be precisely programmed on the basis of wave-front analysis in order to also arrange on the cornea Alvarez surfaces and corrections of aberrations of the individual eye. Due to this additional procedure, the elements for implanting are reduced to an element in the simplest exemplary embodiment. This provides the preferred exemplary embodiment wherein the optical element with a fixed position is formed by the cornea and the optical properties are arranged in the cornea by a laser in the form of a relief surface. It is likewise possible to arrange such a structure on the natural eye lens by means of a laser treatment. The application of this measure is usually precluded, however, because in situations where an intra-ocular eye lens is placed the natural eye lens has usually been removed.

It is also possible to implant into patients a cataract lens provided with an arcuate Alvarez surface which provides accommodation in combination with a second Alvarez component which is fixed to the iris.

The present disclosure also relates to a method for arranging an accommodating intra-ocular artificial lens wherein an optical element is arranged on the cornea via a laser treatment.

Performing of such a laser treatment applies a relief in the external surface of the cornea. This is less desirable from a hygienic and practical viewpoint. A specific preferred exemplary embodiment, therefore, provides the measure that the relief surface is located inside the cornea.

In order to arrange such a structure, a preferred exemplary embodiment provides the measure wherein a disc-shaped outer layer of the cornea is lifted, the relief surface is then formed at the position of the removed layer, and finally the removed layer is folded back again. This lifting of a layer of the cornea is a standard surgical procedure. The arranging of an arcuate Alvarez surface on the cornea is novel.

Modern techniques and materials provide the option of giving the intra-ocular artificial lens according to the present disclosure a thin form. This creates the problem that the lens is limp and the optical surface is deformed by forces exerted on the eye during the accommodation process. This does, of course, result in a deterioration of the optical quality of the lens formed by the optical elements. This is prevented by the measure that the optical elements are provided with strengthening elements which extend on their periphery and with which they acquire the necessary firmness.

The present disclosure provides means which function as a substitute for glasses or contact lenses. People who wear glasses and contact lenses in the armed forces are confronted with challenges in performing their activities. Improvement of eyesight and minimizing the number of people wearing glasses and contact lenses is an important point for defense forces worldwide. The intra-ocular artificial lenses as described in the present disclosure and previous patent applications are highly suitable for this purpose. According to a preferred exemplary embodiment, at least one of the optical elements comprises an optical filter with transmission characteristics dependent on the wavelength of the light. Intra-ocular lenses with filters for ultraviolet light (UV) are now in general use, but other specific wavelengths can also be extinguished. It is noted here that this measure is not only applicable in intra-ocular eye lenses of the type described in the present disclosure, but is also applicable in intra-ocular eye lenses generally.

According to a specific preferred exemplary embodiment, intra-ocular eye lenses can generally be equipped with light filters with extinguishing peaks in the infrared range. High light intensities of military lasers can hereby be blocked; frequencies of these lasers vary in the range of 742-1550 nm for directional and offensive lasers.

It is also possible to apply special transparent photochromes which block all light briefly and within a number of milliseconds at the high light intensities in the visible (400-700 nm) and UV range (300-360 nm) during explosions.

The principle forming the basis of the present disclosure requires the use of at least two optical elements. The inventor has found that, when two optical elements are used, the optical elements can be given an identical form. This is advantageous from a production engineering viewpoint. It is noted here that this measure is not only applicable to the optical elements themselves but also to the elements connected to the optical elements. The two optical elements are, of course, here positioned rotated relative to each other over two different axes.

A further reduction in costs occurs when the optical elements, the flexible and the rigid connecting elements and the anchors are manufactured from the same material. This measure provides the option of manufacturing all these elements in the same forming process, such as, for instance, turning and cutting or injection molding. It is, however, also possible to manufacture the optical elements and the other components from different materials. The choice of material can be optimized for any function.

Cell growth-inhibiting agents for inhibiting the activity of fibrogenic cells and thus preventing PCO are not yet applied in combination with intra-ocular lenses. Rapamycin, for instance, (also known as sirolimus) is a generally known cell growth-inhibiting pharmaceutical product in use in organ transplantation and treatment of different disorders of the eye (including, but not limited to, melanoma, uveitis and infections of the cornea). For ophthalmic applications, we refer here to International Patent Publication No. WO 2005/027906, U.S. Patent Publication No. 2005/064010, International Patent Publication No. WO 2005/011813 and Japanese Patent Application No. 5194212.

Rapamycin is suitable for preventing PCO and hardening of the lens capsule by inhibiting general cell growth close to an intra-ocular lens, inhibiting transformation of epithelial cells to fibroblasts and inhibiting further fibrogenic activity. Rapamycin is approved for use in the eye. Other possible candidates for such a therapeutic are mitomycin, cyclosporin toramycin preparations and the like. Mitomycin is already applied as an inhibitor of fibroblast growth elsewhere in the eye. Corticosteroids and even specific cytostatic preparations could also be suitable for such an application.

According to a further preferred exemplary embodiment of the present disclosure, the intra-ocular artificial lens is coupled to a therapeutic. This therapeutic can be formed by rapamycin, but equally by another therapeutic.

The therapeutic is preferably arranged in a carrier which simplifies administering. This carrier can take the form of an encapsulation of the therapeutic, but the carrier can likewise be formed by a matrix incorporating the therapeutic.

The therapeutic is preferably received in its carrier such that the therapeutic is released slowly.

The carrier can be received in an element of the intra-ocular artificial lens. This results in a simple procedure for placing of the combination of artificial lens and therapeutic. In this case, the carrier can be formed by the polymer mass of at least one of the parts of the artificial lens.

It is, however, also possible for the carrier to be accommodated on one of the surfaces of the intra-ocular artificial lens. Surfaces with an optical function must be avoided as much as possible here.

It is, however, also possible for the carrier to be formed by a separate element which is adapted for placing simultaneously with the placing of the intra-ocular artificial lens. This exemplary embodiment provides the option of adapting the nature and dosage of the therapeutic to the situation encountered during placement of the intra-ocular artificial lens.

According to a more specific exemplary embodiment, the therapeutic is formed by rapamycin. Rapamycin can also be incorporated in the above-stated manner in all other existing intra-ocular lenses and related products. The effect of rapamycin has advantages for the mechanical operation of the present lenses, and PCO can be prevented in all ophthalmic products.

The therapeutic can also be inserted, independently of the artificial lens but during the surgical treatment, particularly on the rear side of the artificial lens.

BRIEF DESCRIPTION OF THE DRAWINGS

Various aspects of the present disclosure are described hereinbelow with reference to the accompanying figures.

FIG. 5 is a perspective view of the optical element shown in FIGS. 3A and 3B;

FIG. 6 shows a perspective view of an exemplary embodiment wherein both optical elements are combined in a construction for implantation on the front side of the iris;

FIG. 7 shows a cross-sectional view of an exemplary embodiment with a fixed optical element and a displacing element; and FIG. 8 is a cross-sectional view of a variant of the exemplary embodiment shown in FIG. 7 with a fixed optical element and a displacing optical element.

DETAILED DESCRIPTION

Figure 1A:
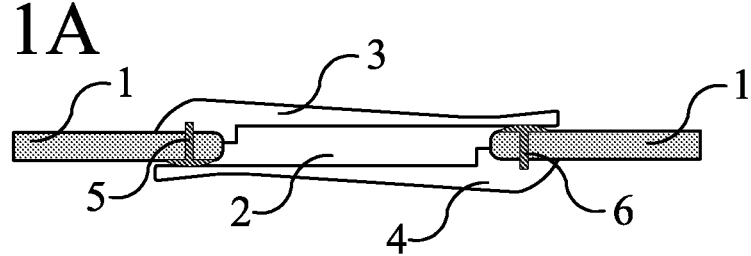
FIG. 1A shows a cross-sectional view of a first exemplary embodiment in the case of a large pupil.

FIG. 1A shows a cross-sectional view of an iris 1 which encloses pupil 2. The intra-ocular lens according to the present disclosure comprises two optical elements 3, 4 which are preferably, though not necessarily, identical. The first optical element 3 is connected by means of a nail 5 to one side of iris 1, while the second optical element 4 is connected by means of a nail 6 to the other side of the iris. Nails 5, 6 are arranged on the front side and rear side, respectively, of the iris. FIG. 1A shows a relatively dark situation with a large pupil 2 and a wide open iris 1. The optical elements are preferably formed here for near vision.

Figure 1B:
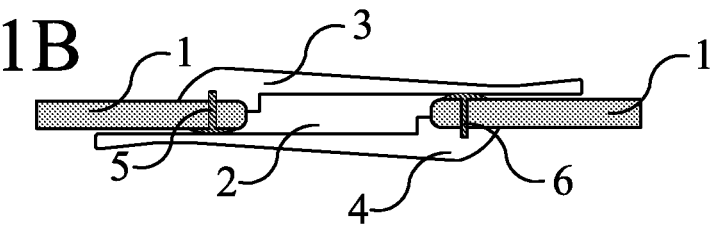
FIG. 1B shows a view corresponding with FIG. 1A in the case of a small pupil.
Figure 1C:
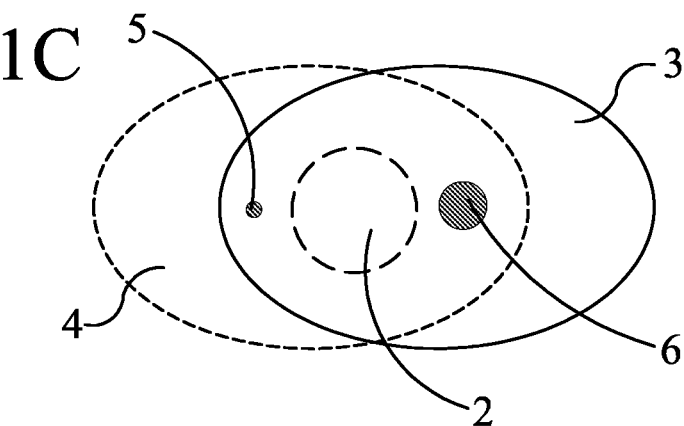
FIG. 1C is a schematic front view of the first exemplary embodiment shown in FIGS. 1A and 1B.

FIG. 1B shows the same device but in a light situation, wherein pupil 2 is small and iris 1 is contracted. Optical elements 3, 4 are preferably adapted for distance vision. This latter situation is shown in a front view in FIG. 1C. It is otherwise possible to place nails 5, 6 with their heads on the same side, for instance, the rear or front side, of the iris.

Figure 2A:
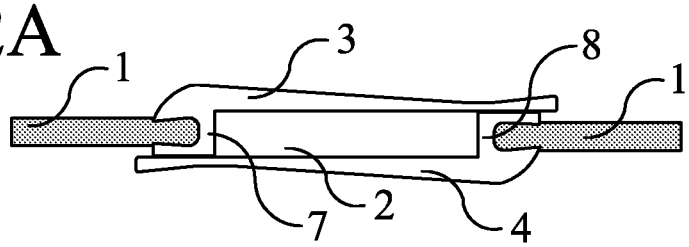
FIG. 2A shows a cross-sectional view corresponding with FIG. 1A of a first variant.
Figure 2B:
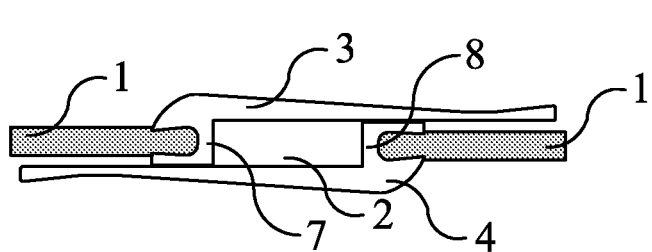
FIG. 2B shows a cross-sectional view corresponding with FIG. 1B of a first variant.

FIG. 2A shows a situation corresponding to FIG. 1A, wherein optical elements 3, 4 are connected to iris 1 not by a nail but by a clamp 7, 8 respectively. This shows the relatively dark situation. The relevant light situation is shown in FIG. 2B.

It is possible in principle to apply other types of attachment between iris 1 and optical elements 3, 4. FIGS. 3A-5 thus show a situation in which fixation is obtained between optical elements and 3, 4 and iris 1 with a claw-like hook 9, 10, respectively. These claw-like hooks 9, 10 make it possible to give clamps 7, 8 a smaller form. An advantage of this configuration is that the transmission of forces between iris 1 and the optical elements is distributed over different parts of the iris which is formed by a delicate tissue.

Figure 3A:
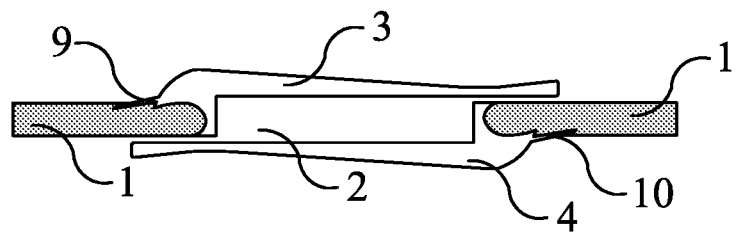
FIG. 3A shows a cross-sectional view corresponding with FIGS. 1A and 2A of a second variant.
Figure 3B:
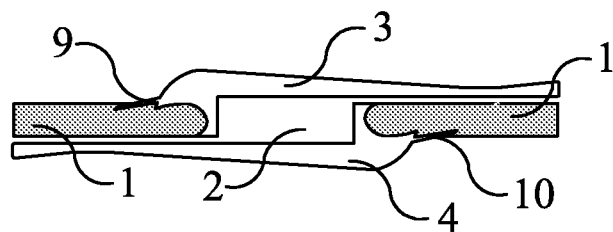
FIG. 3B shows a cross-sectional view corresponding with FIGS. 1B and 2B of a second variant.
Figure 4A:
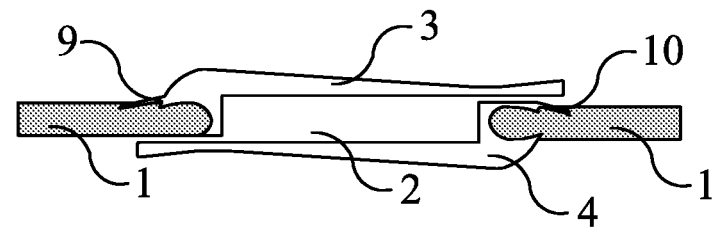
FIG. 4A shows a cross-sectional view corresponding with FIGS. 1A and 2A of a third variant.
Figure 4B:
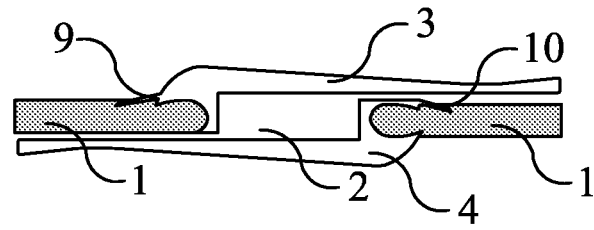
FIG. 4B shows a cross-sectional view corresponding with FIGS. 1B and 2B of a third variant.

FIGS. 3A-3B show perhaps the simplest exemplary embodiment of this concept. FIGS. 4A-4B show an exemplary embodiment wherein the hooks of both optical elements are situated on the front side of the iris which simplifies the implantation and perhaps the removal of the optical elements by the surgeon.

The same situation is shown in FIG. 5 in the form of a perspective view. The orbicularis muscle 1a for driving the movements of iris 1 is shown here in the form of a torus. FIG. 5 only shows an element on the upper side of the iris. The other element is not shown but is situated on the underside of the orbicularis muscle (torus).

It is pointed out that, in the above shown configuration, optical elements 3, 4 are each placed on one side of the iris in all cases. It is, of course, possible to place both optical elements on the same side of the iris, i.e., in front of or behind the iris.

FIG. 6 shows a perspective view of a configuration wherein use is made of positioning means as described earlier in Netherlands Patent Application No. 1028496. In this earlier patent application these positioning means are arranged in the lens capsule. In the situation shown in FIG. 4, however, the entity of optical elements and positioning means is arranged in the anterior chamber, i.e., on the front side of the iris. Optical elements 3, 4 are mutually connected here on one side via resilient constructions 11 and on another side with a rigid connection 12. This enables a relative displacement of the optical elements. On both sides of the overall construction, a claw or hook connection is arranged for fixing to the iris.

FIG. 7 shows a cross-section of an exemplary embodiment wherein an optical element 3 occupies a fixed position, in this example supported by chamber corners 13 of the anterior chamber and behind cornea 15. The other element 4 is fixed to the iris, in this example with a nail connection 5.

FIG. 8 shows a variant of the exemplary embodiment depicted in FIG. 7 wherein fixed element 3 is combined with a moving element 4 fixed to two sides of iris 1 with, in this example, a claw connection 14. The resilient connection 11 and the rigid connection 12 enable displacement of element 4, driven by iris 1, relative to element 3.

All patents, patent applications and publications referred to herein are incorporated by reference in their entirety.

The invention claimed is:

1. An intra-ocular artificial lens with variable optical strength, comprising:
   at least two optical elements, at least one of which is movable relative to at least one other element in a direction extending transversely to the optical axis, at least one of the optical elements having an optical thickness according to the formula $$t = A(xy^2 + x^3/3)$$

where
   t is the optical thickness of the optical element in the direction of the optical axis,
   x is the coordinate in the direction of the motion of the optical elements,
   y is the coordinate in the direction perpendicular to the optical axis and to the x-direction, and
   A is a constant,
   wherein the optical elements have a form such that in different relative positions of the optical elements the artificial lens has different optical strengths, and
   wherein each of the movable optical elements is connected to two positioning means which are adapted for coupling to the iris of the eye.

2. The intra-ocular artificial lens of claim 1, wherein the positioning means are adapted to cause the optical elements to make a translating movement relative to each other during movement of the iris.

3. The intra-ocular artificial lens of claim 1, wherein the positioning means are adapted to cause the optical elements to make a rotating movement relative to each other during movement of the iris.

4. The intra-ocular artificial lens of claim 1, wherein at least one of the positioning means is connected to mechanical arresting means for limiting the stroke of each movable optical elements.

5. The intra-ocular artificial lens of claim 1, wherein the positioning means are adapted for forming by the optical elements at a small pupil diameter of a lens with a strong dioptric value and for forming by the optical elements at a large pupil diameter of a lens with a weak dioptric value.

6. The intra-ocular artificial lens of claim 5, wherein the optical elements are adapted to form a lens with a negative dioptric value at a large diameter of the pupil.

7. The intra-ocular artificial lens of claim 1, wherein the optical elements are adapted to correct aberrations of the eye.

8. The intra-ocular artificial lens of claim 7, wherein the optical elements are adapted to correct astigmatic aberrations of the eye.

9. The intra-ocular artificial lens of claim 1, wherein the optical elements are arranged at a distance from each other.

10. The intra-ocular artificial lens of claim 1, wherein one of the optical elements is positioned on the front side of the iris and the other optical element is positioned on the rear side of the iris.

11. The intra-ocular artificial lens of claim 1, wherein each of the positioning means of each of the optical elements is connectable to the iris.

12. The intra-ocular artificial lens of claim 11, wherein the optical elements are connectable to the iris on one of their sides.

13. The intra-ocular artificial lens of claim 11, wherein the optical elements are connectable to the iris at more than one location around the pupil.

14. The intra-ocular artificial lens of claim 11, wherein the optical elements are couplable to the iris with a nail connection.

15. The intra-ocular artificial lens of claim 14, wherein the heads of the nail connections of both optical elements are situatable on the rear side of the iris.

16. The intra-ocular artificial lens of claim 11, wherein the optical elements are couplable to the iris with a clamp connection.

17. The intra-ocular artificial lens of claim 11, wherein the optical elements are couplable to the tissue of the iris with a claw or hook connection.

18. The intra-ocular artificial lens of claim 17, wherein the claw or hooks of the connections of both optical elements are situatable on the front side of the iris.

19. The intra-ocular artificial lens of claim 1, wherein at least one optical element is situatable between the iris and the cornea.

20. The intra-ocular artificial lens of claim 1, wherein at least one optical element is situatable between the iris and the lens capsule.

* * * * *